(12) United States Patent
Moore-Smith et al.

(10) Patent No.: US 6,534,095 B1
(45) Date of Patent: *Mar. 18, 2003

(54) PULSATILE ACIDIFICATION WAVE DEMINERALIZATION PROCESS FOR PRODUCING OSTEOINDUCTIVE BONE; AND OSTEOINDUCTIVE BONE PRODUCED THEREBY

(75) Inventors: Debra Moore-Smith, Chesapeake, VA (US); Robert K. O'Leary, Deltaville, VA (US); Anne Wilson, Virginia Beach, VA (US)

(73) Assignee: LifeNet, Virginia Beach, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/655,711

(22) Filed: Sep. 5, 2000

Related U.S. Application Data

(60) Provisional application No. 60/152,272, filed on Sep. 3, 1999.

(51) Int. Cl.$^7$ .......................... A61K 35/32; C12N 5/00; A01N 1/00; C12M 1/34; C12M 1/36
(52) U.S. Cl. ................... 424/549; 435/378; 435/284.1; 435/286.5; 435/288.1
(58) Field of Search .......................... 424/549; 435/378, 435/284.1, 286.5, 288.1

(56) References Cited

U.S. PATENT DOCUMENTS 6,189,537 B1 * 2/2001 Wolfinbarger, Jr.

* cited by examiner

*Primary Examiner*—Christopher R. Tate
(74) *Attorney, Agent, or Firm*—Susanne M. Hopkins

(57) ABSTRACT

The invention is directed to a process for producing demineralized osteoinductive bone, and demineralized osteoinductive bone produced thereby. The process achieves demineralization of bone by subjecting bone, including for example ground bone, bone cubes, chips, strips, or essentially intact bone, to a rapid high volume, pulsatile acidification wave process. The process includes subjecting bone to two or more rapid pulse/drain cycles where one or more demineralizing acids are rapidly pulsed into a vessel containing bone, and after a desired period of time, is rapidly drained from the vessel, the vessel containing the bone is then rapidly refilled with the one or more demineralizing acids (pulsed). The process allows bone to be rapidly demineralized to a precise ans specific desired residual calcium level, without sacrificing osteoinductivity.

39 Claims, 2 Drawing Sheets

PULSATILE ACIDIFICATION WAVE DEMINERALIZATION PROCESS FOR PRODUCING OSTEOINDUCTIVE BONE; AND OSTEOINDUCTIVE BONE PRODUCED THEREBY

This application claims benefit of provisional application No. 60/152,272 filed Sep. 3, 1999.

FIELD OF THE INVENTION

The invention is a process for producing demineralized osteoinductive bone, and demineralized osteoinductive bone produced thereby. The process achieves demineralization of bone by subjecting bone, including for example ground bone, bone cubes or strips, and essentially intact bone, to a rapid high volume, pulsatile acidification wave process. The process allows bone to be rapidly demineralized to a precise and specific desired residual calcium level, without sacrificing osteoinductivity.

BACKGROUND OF THE INVENTION

Demineralized freeze-dried bone allograft is widely used in the repair of skeletal defects and periodontal disease. It is known that the implantation of acid demineralized bone in the form of a powder in extraskeletal sites may stimulate new bone formation. Various groups including Syftestad, 1982; Urist et al., 1967; Urist and Strates, 1979; Urist and Strates, 1971; Urist et al., 1983; have suggested that a noncollagenous protein or proteins present in demineralized bone has the ability to induce new bone formation when present within the implanted bone matrix.

Current procedures used to demineralize ground bone involve the use of ethanol to remove lipids and hydrochloric acid to remove the mineral components of bone. These known methods are problematic in that they require prohibitively long periods of time for processing resulting in a very low demineralization rate; require excessive handling of the ground bone being processed; are capable of processing only small amounts of ground bone; and result in a demineralized bone product which exhibits inferior osteoinductivitiy caused by excessive exposure of bone inducing proteins in the bone to harsh acids over extended periods of time.

SUMMARY OF THE INVENTION

The invention achieves high demineralization rates by subjecting bone, for example ground cortical bone, to rapid and complete exchanges of acid. Suitable acids include both highly ionized and/or weak acids. The inventors have discovered that the acid neutralization rate of bone mineral apatite is highly dependent upon the bone surface concentration of the acid and the demineralization reaction products. The initial reaction rate of the acid at the surface of the bone particle is very rapid and quickly terminates, due to boundary layer resistance caused by the increasing concentrations of the reaction by-products, if the residual reaction products are not promptly removed. Since the bone is subjected to the demineralizing acid for very brief periods of time, bone-inducing proteins are not adversely affected, thus resulting in a bone product, which achieves maximum potential osteoinductivity. The process also allows the demineralization of an entire single donor's tissue volume in a single batch.

The invention provides a rapid demineralization process for producing osteoinductive bone. including subjecting bone to two or more pulse and drain exchanges of a predetermined volume of one or more demineralizing acid solutions to produce demineralized bone.

The invention also provides a rapid demineralization process for producing osteoinductive bone, including subjecting bone to two or more pulse and drain exchanges of a predetermined volume of one or more demineralizing acid solutions under conditions effective to produce demineralized bone.

The invention further provides a rapid demineralization process where each of the pulse and drain exchanges, include rapidly pulsing a predetermined volume of one or more demineralizing acid solutions into the container, incubating the bone and the predetermined volume of one or more demineralizing acid solutions in the container for an interval of time, and rapidly draining the predetermined volume of one or more demineralizing acid solutions from the container.

The invention also provides a rapid demineralization process for producing osteoinductive demineralized bone, including placing an amount of bone to be demineralized into a substantially closed container, and cycling the bone in the substantially closed container through two or more pulse and drain cycles to produce osteoinductive demineralized bone, each of the two or more pulse and drain cycles, including rapidly pulsing a predetermined volume of one or more demineralizing acid solutions into the container, incubating the bone and one or more demineralizing acid solutions in the container for an interval of time, and rapidly draining the predetermined volume of one or more demineralizing acid solutions from the container.

The invention provides a rapid demineralization process where the step of incubating includes agitation including for example, stirring, shaking, orbital shaking, and/or sonicating.

The invention provides a rapid demineralization process for demineralizing bone by subjecting bone to two or more rapid fill and drain pulses of one or more of the following: a demineralizing acid, and a cation extractor including for example one or more metal chelators or electrolyte solutions.

The invention provides a rapid demineralization process for demineralizing bone by subjecting bone to two or more changes of one or more demineralizing acids, under conditions sufficient to achieve a demineralization rate of from about 1.5 g demineralized bone per minute to about 30.0 g per minute, preferably form about 5.0 g per minute to about 30.0 g per minute, more preferably from about 8.0 g per minute to about 25.0 g per minute, and most preferably from about 10.0 g demineralized bone per minute to about 22.0 g per minute.

The invention further provides a rapid demineralization process for demineralizing bone where the fill and drain pulses are carried put over intervals of from about 1.0 minutes to about 30 minutes, preferably from about 2.0 minutes to about 25.0 minutes, and more preferably from about 3.0 minutes to about 20.0 minutes, and most preferably about 5.0 minutes.

The invention also provides a rapid demineralization process for demineralizing bone where rapid acid pulse or rapid acid drain is achieved over a time period of from about 0.5 minutes to about 8 minutes, preferably from about 0.5 minutes to about 2.0 minutes to rapidly fill (pulse) the vessel with acid, more preferably about 1.0 minutes to pulse the acid; and preferably about 1.0 to about 10.0 minutes to drain acid, and more preferably from about 2.0 minutes to about 5.0 minutes to drain the acid.

The invention also provides a rapid demineralization process for demineralizing bone by subjecting bone to two or more rapid fill and drain pulses of one or more acid solutions where the bone is demineralized until a specific desired residual calcium level is achieved.

BRIEF DESCRIPTION OF THE FIGURES

The invention is further explained in the description which follows with reference to the figures and drawings, by way of non-limiting examples, various embodiments of the invention, with like reference legends representing similarly collected data throughout the sever figures and drawings.

FIG. 1 illustrates an embodiment of the apparatus used for demineralizing bone according to the inventive process.

FIG. 2 illustrates a preferred embodiment of the inventive apparatus for demineralizing bone according to the inventive process.

FIG. 3 illustrates a side view or the present filter assembly.

DESCRIPTION OF THE PREFERRED EMBODIMENTS

I. Definitions

Figure 1:
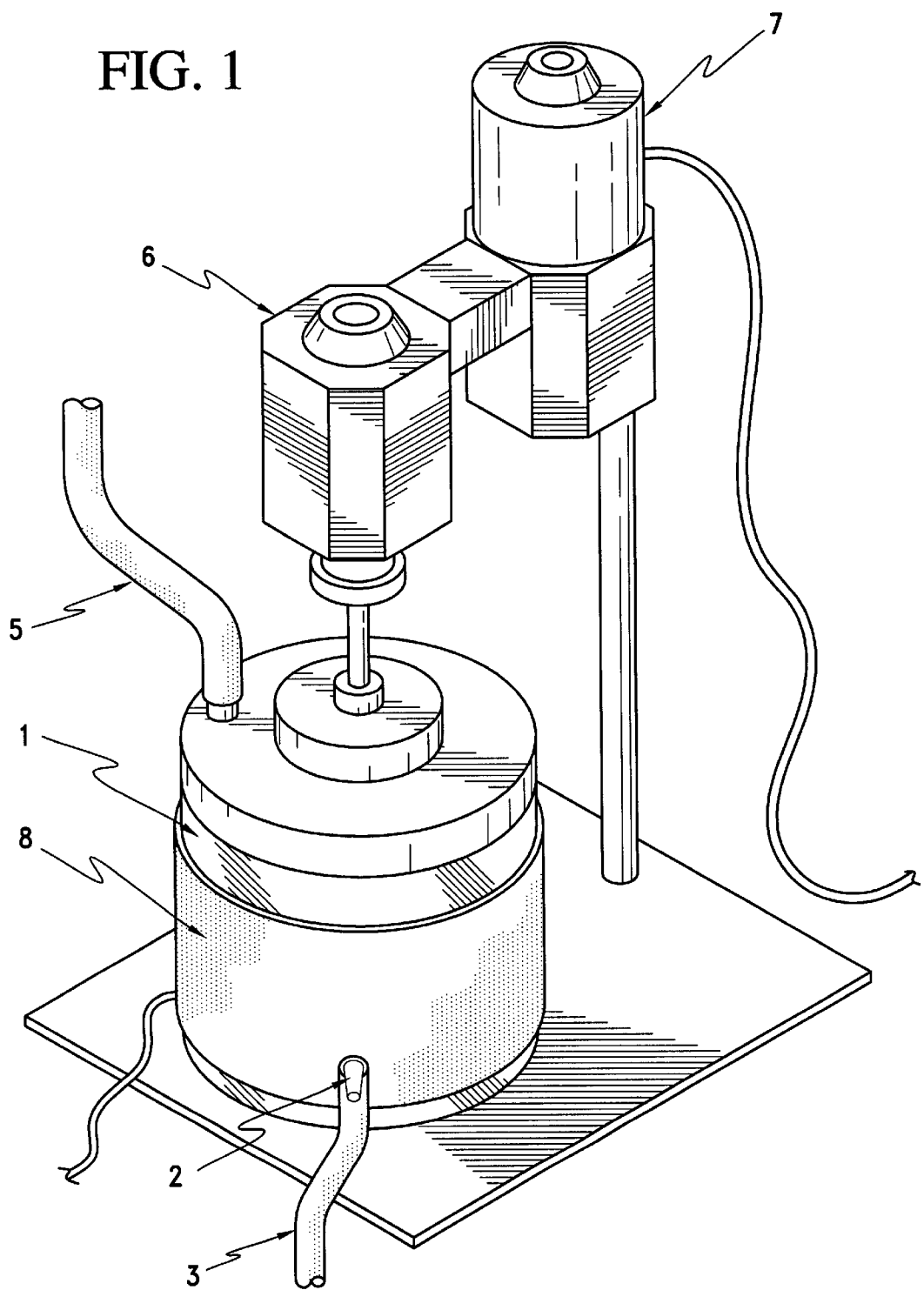
FIG. 1.

The below definitions serve to provide a clear and consistent understanding of the specification and claims, including the scope to be given such terms.

Acid. By the term "acid" is intended any acid or acid solutions containing one or more acids, capable of demineralizing bone including for example, highly ionizable acids including but not limited to hydrochloric acid; and weakly ionizable acids including but not limited to citric acid. Such acid solutions may also include solutions of one or more acids in one or more alcohols, such alcohols including for example ethanol, and IPA, and solutions of one or more acids in glycerol or other organic and/or inorganic metal remover, i.e. metal chelator. Suitable acids include but are not limited to: formic acid, acetic acid, citric acid, propionic acid (organic acid), hydrochloric acid, phosphoric acid (inorganic acid); physiological tissue compatible hydroxy carboxylic acids including for example but not limited to: citric acid, gluconic acid, malic acid, tartaric acid, fumaric acid, and phosphoric acid; combinations which chelate calcium; and/or amino carboxylic agents including chelators including for example ethylenedediaminetetracetic acid (EDTA) (or analogues of this chelator), NTA, citric acid, succinic acid, and heparin can be used to chelate (bind) calcium which aids in the demineralization of bone by both organic and inorganic acids. Hydroxy carboxylic acids alone or in combination with amino carboxylic agents are advantageous for use in the demineralization process because they reduce the hydrolytic attack on bone morphogenic proteins present in the bone and because they are antioxidants which antioxidants serve as preservatives of the bone, thus eliminating the need for freeze drying the bone to preserve it.

Allowash™ Solution. By the term "Allowash™ solution" is intended for the purposes of this invention those detergent compositions disclosed in U.S. Pat. No. 5,977,034, incorporated herein by reference. Examples of suitable Allowash™ compositions include: a cleaning composition containing about 0.06 wt % polyoxyethylene-4-lauryl ether; about 0.02 wt % poly (ethylene glycol)-p-nonyl-phenyl-ether; about 0.02 wt % octylphenol-ethyleneoxide and endotoxin free deionized/distilled water.

Bone. By the term "bone" is intended for the purposes of the invention, autograft bone, allograft bone and xenograft bone. Such bone includes any bone from any source, including for example, human bone for example from: a living donor, or a cadaveric donor, and animal bone. The bone may include cortical bone and/or cancellous bone and/or cortico cancellous bone, in any form including for example, ground bone, particulate bone (i.e. dental bone) preferably in the particle size range of from about $120\mu$ to about $860\mu$, bone chips, bone strips, bone cubes, and essentially intact bone.

Bone Marrow Elements. By the term "bone marrow elements" is intended the highly cellular hematopoietic connective tissue filling the medullary cavities and spongy epiphyses of bones which may harbor bacterial and/or viral particles and/or fungal particles, and includes, for example blood and lipid.

Cycle. By the term "cycle" is intended one complete rotation of the tray of an orbital shaker, including for example orbital shaker by Troemner, Inc., model 980001, Serial No: 1035; 500 watts, this orbital shaker is preferably operated at a setting of from about 150 to about 210, more preferably from about 160 to about 170, which settings correlate to about from 20 to about 60 cycles/min.

Detergent. By the term "detergent" is intended any agent which through a surface action that depends on it possessing both hydrophilic and hydrophobic properties and/or exerts oil-dissolving (cleansing) and/or antibacterial and/or antiviral effects, and can include but is not limited to: anionic detergents, cationic detergents, acridine derivatives, long-chain aliphatic bases or acids, and Allowash™ detergent solutions.

Disinfectant. By the term "disinfectant" is intended one or more decontaminating agents which remove or inactivate/ destroy and infectious material potentially present in the bone marrow of a bone graft; including for example, bacteria, virus and/or fungi; with such decontaminating agents including for example, an antibacterial agent; an antiviral agent; an antimycotic agent; an alcohol including for example, methyl, ethyl, propyl, isopropyl, butyl, an/or t-butyl; trisodium phosphate; sodium hydroxide; hydrogen peroxide; and/or and detergent.

Drain. By the term "drain" is intended for the purposes of this invention, rapidly and substantially completely, draining a volume of one or more demineralizing acids from a substantially closed processing container. Preferably, the demineralizing acid is substantially completely drained from the processing container in less than 10.0 minutes, more preferably in less than 9.0 minutes.

Lipid. By the term "lipid" is intended the fat-soluble constituents of bone marrow, including for example fatty acids, glycerides, and phospholipids.

Pulse. By the term "pulse" is intended for the purposes of this invention, rapidly and substantially completely, filling a substantially closed processing container with a predetermined volume of one or more demineralizing acids or acid solutions. Preferably, the container is substantially completely filled with the predetermined volume of demineralizing acid in less than 3.0 minutes, more preferably in less than 2.0 minutes.

Solvent. By the term "solvent", is intended for the purposes of the invention, a liquid cleaning composition capable of: facilitating the solubilization of lipid, facilitating bone marrow removal, inactivating viral and/or bacterial particles, and/or disrupting cell membranes, and/or demineralizing bone, which may contain, but is not limited to, one or more of the following: water; saline; a detergent; a disinfectant; an acid; an alcohol, for example, ethanol and/or isopropanol; solvents; a combination of solutes desired to facilitate solubilization of bone marrow, including for example Allowash™ detergent solutions; a chelating agent; a bactericidal agent; an antimycotic agent; sodium hydroxide or similar strong base; organic and/or inorganic acid known and used in the art for the demineralization of bone including for example hydrochloric acid; and/or hydrogen peroxide. Known lipophilic solvents include for example, ethanol and chloroform.

Substantially Closed Processing Container. By the term "substantially closed processing container" is intended for the purposes of the present invention, any rigid or deformable container or reservoir of a size sufficient to contain bone and a predetermined volume of one or more demineralizing acids, composed of a material that is stable when in contact with the demineralizing acids, and is configured to allow the rapidly pulsing of a solution into the container and to allow the rapid draining of a solution from the container.

Undesirable Constituents. By the term "undesirable constituents" is intended for the purposes of the present invention any constituents normally associated with a particular tissue whose presence in that tissue to be transplanted is undesirable, for example, blood cells; bacteria; fungi; viruses; in the case of bone, bone marrow elements including lipid and blood, and any other constituents normally associated with bone marrow as well as any bacterial, viral or fungal contamination associated with the bone and/or bone marrow elements.

Filter Mesh. By the term "filter mesh" is intended for the purposes of the invention, any mesh composed of a material stable in the presence of the demineralizing solution having a mesh size sufficiently small so as to exclude bone particles. Suitable filter mesh includes polyester monofilament having a mesh size of from $100\mu$ to about $300\mu$, preferably from about $100\mu$ to about $225\mu$, and most preferably about $125\mu$. Such filter mesh includes Pes125, manufactured by Industrial Fabrics Corp., Minneapolis Minn., which is a polyester monofilament mesh having a mesh size of $125\mu$.

The inventive process allows for the decalcification of an entire single donor's tissue volume in a single vessel over a tissue weight range of 100 to 800 grams or more, at a rapid demineralization rate, over a short period of time. The bone produced is uniformly demineralized and optimally osteoinductive.

II. Procurement and Processing of Bone

Bone is procured and processed according to methods well known in the art to which the invention pertains. For example, bone is procured from a cadaver donor, cleaned of soft tissue, and bone marrow elements and undesirable constituents are removed. The bone is then processed to a desired form including for example, ground into particulate bone, cut into cubes or strips, or left essentially intact. Bone is procured and processed under conditions according to accepted industry standards. Both cortical and/or cancellous bone is suitable for use in the inventive process.

III. Demineralization of Bone

Using the inventive process, bone is demineralized with acid, including for example relatively strong acids such as hydrochloric acid at concentration sufficient to demineralize bone, for example fo from about 0.1N to about 3.0N and relatively weak acids including for example, citric acid at concentrations sufficient to demineralize bone, for example of from about 0.5N to about 5.0N. The acid, for example, citric acid, may be dissolved in one or more lipid soluble alcohols containing permeation enhancement surfactants to enhance the chemical reactivity and physical penetration of the acid into the mineral apatite of the bone. Weak acids including citric acid may be used in combination with low concentrations of strong acids including for example hydrochloric acid, to provide a demineralization system in which a desired pH, for example a pH of 1.2 which pH has been found to correlate to a residual calcium level of about 2.0 wt %, could not be exceeded, thus eliminating the potential of over decalcifying the bone matrix.

The rate of demineralization, i.e. grams of bone demineralized per minute, can be increased or decreased as desired, by one of ordinary skill in the art to which the present invention pertains and without undue experimentation, based on factors which include: the reaction temperature; the concentration or normality of the acid and the acid's neutralization potential (strong or weak) in reacting with $Ca++$ hydroxy apatite; the acid's dissociation or percent ionization; the delivery rate of the acid to the bone or the bone to the acid; the mass, volume and density of the bone to be demineralized; the concentration of the calcium hydroxyapatite in the bone; the degree to which the bone has been cleaned of fat and protein; the surface area of the bone particles and their particle size distribution; the compaction of the bone upon contact with the acid by the action of the acid on the bone and the rate at which the products are removed from the acid; the method of agitation, i.e. mechanical stirring; shaking; orbital shaking; sonication; as well as other methods of agitation which provide uniform concentration of the reacting species and reduction of boundary layer resistance; and the degree to which a boundary layer resistance forms on the microporous surface of the bone particle and the packing of these particles with each other. Accordingly, the demineralization rate can be increased for example, by increasing any one or more of the foregoing factors, for example, by increasing the temperature, acid concentration; surface area of the bone to be demineralized; and increasing agitation. Likewise, the demineralization rate can be decreased by decreasing any one or more of the foregoing factors, for example, decreasing the acid concentration, slowing the delivery of acid, increasing bone particle size, etc.

(A) Determining a Desired Residual Calcium Level

The rapid demineralization inventive process is stopped when a desired residual calcium level of calcium in the bone matrix being demineralized has been reached. U.S. patent application Ser. No: 08/706,707, filed Sep. 6, 1996, now allowed, is directed to methods for producing osteoinductive bone, and osteoinductive bone produced, and is hereby incorporated herein by reference in its entirety. To determine a stopping point, a particular pH of eluent acid which correlates with the desired residual calcium level, must be determined. This is done by first obtaining a bone sample and determining the initial calcium concentration of the bone according to methods well known in the art to which the invention applies; demineralizing bone at a constant rate; simultaneous with demineralizing, periodically sampling the acid solution and the bone from the closed reaction container at specific intervals of time during the demineralization process; determining the pH of each sample of acid solution and determining the residual calcium level of each corresponding bone sample; plotting the pH of a sample versus the calcium concentration of the corresponding bone sample, and drawing a curve; and from the curve determining what pH of the acid correlates with the desired residual calcium level. Thereafter, the residual calcium level of a bone sample can be determined by determining the pH of a sample of the acid solution, sampled at a time point during demineralization of the bone sample, by determining the calcium concentration on the curve which corresponds to the pH of the acid sample.

(B) Determining the Amount of Acid and Number of Pulse/Drain Cycles:

A preferred method for determining the amount of acid needed, and the number of pulse/drain cycles needed is as follows: The weight of the ground bone is first determined. Thereafter, the donor weight in grams is divided by 100 grams and the resultant number is multiplied by 3 liters. This is the total volume of acid needed to demineralize the given amount of ground bone.

Next, the number of pulse/drain cycles is calculated. The total volume of acid calculated is divided by 4. This number is the number of pulse/drain cycles needed. Each pulse/drain cycle is carried out with 4 liters of acid.

For example if the amount of ground bone is 425 grams, this number is divided by 100 grams which equals 4.25 which is then multiplied by 3 liters to yield a total acid volume of 12.75 liters. This number is then divided by 4 to yield 3.19 pulse/drain cycles. Thus, for 425 grams of bone, 12.75 liters of acid is needed, and processing includes 3 pulse/drain cycles using 4 liters each, and a forth pulse/drain cycle using 0.75 liters of acid (the remainder).

In this calculation, there must be at least two pulse/drain cycles, and each cycle must include an at least 5.0 min. incubation. This calculation is specific for 0.5N HCL, and for reaching 2% residual calciun. Other acids and desired calcium levels can be used, by monitoring the calcium levels during demineralization at specific time points and plotting a curve to determine how much acid is used to reach a specific calcium level.

IV. FIG. 1

FIG. 1 illustrates the apparatus of the invention. Bone is demineralized by placing bone, for example ground bone, in reaction vessel 1 containing a demineralization solution, for example one or more acids at a concentration sufficient to demineralize bone, and in a volume sufficient to process the amount of bone to be demineralized, for example from about 2.0 to about 8.0 liters, preferably from about 3.0 to about 6.0 liters of acid, optionally including heating blanket 8. Thereafter, a defoaming agent is added to the vessel through inflow tubing 5 connected to inlet 4. Suitable defoamers include any defoamers well known in the art to which the invention pertains, and include for example ethanol, for example 60 mls of 200 proof ethanol in 6.0 liters of acid. The bone-acid-ethanol solution is then preferably vigorously agitated, such agitation including for example stirring at from about 500 rpm to about 2500 rpm, preferably 1000 rpm to about 2000 rpm, and more preferably stirred at about 1350 rpm with mixing paddle 6, for example Cole Palmer Model No: E-04541-00 303/304 supplied by Cole Palmer Instrument Co., Vernon Hills, Ill.; while the system is maintained at a desired temperature, for example of from about 0° C. to about 100° C., preferably from about 15° C. to about 50° C., more preferably from about 20° C. to about 40° C., and most preferably at about 23° C. The paddle 6 is driven by a motor 7. After an initial period of time, for example, five minutes, substantially all, for example 90% to 95%, of the acid is then rapidly drained from vessel 1 through outlet port 2 and outflow tubing 3. Vessel 1 was then refilled with the demineralizing solution, and the contents of the vessel was stirred at for example 1350 rpm for a second period of time for example about ten minutes. The vessel 1 was again rapidly drained, refilled and stirred for a third period of time, for example 20 minutes. The acid was then drained and a buffer solution was added to vessel 1 through inlet port 4 and inflow tubing 5, to stop the demineralizing reaction.

FIG. 2

Figure 2:
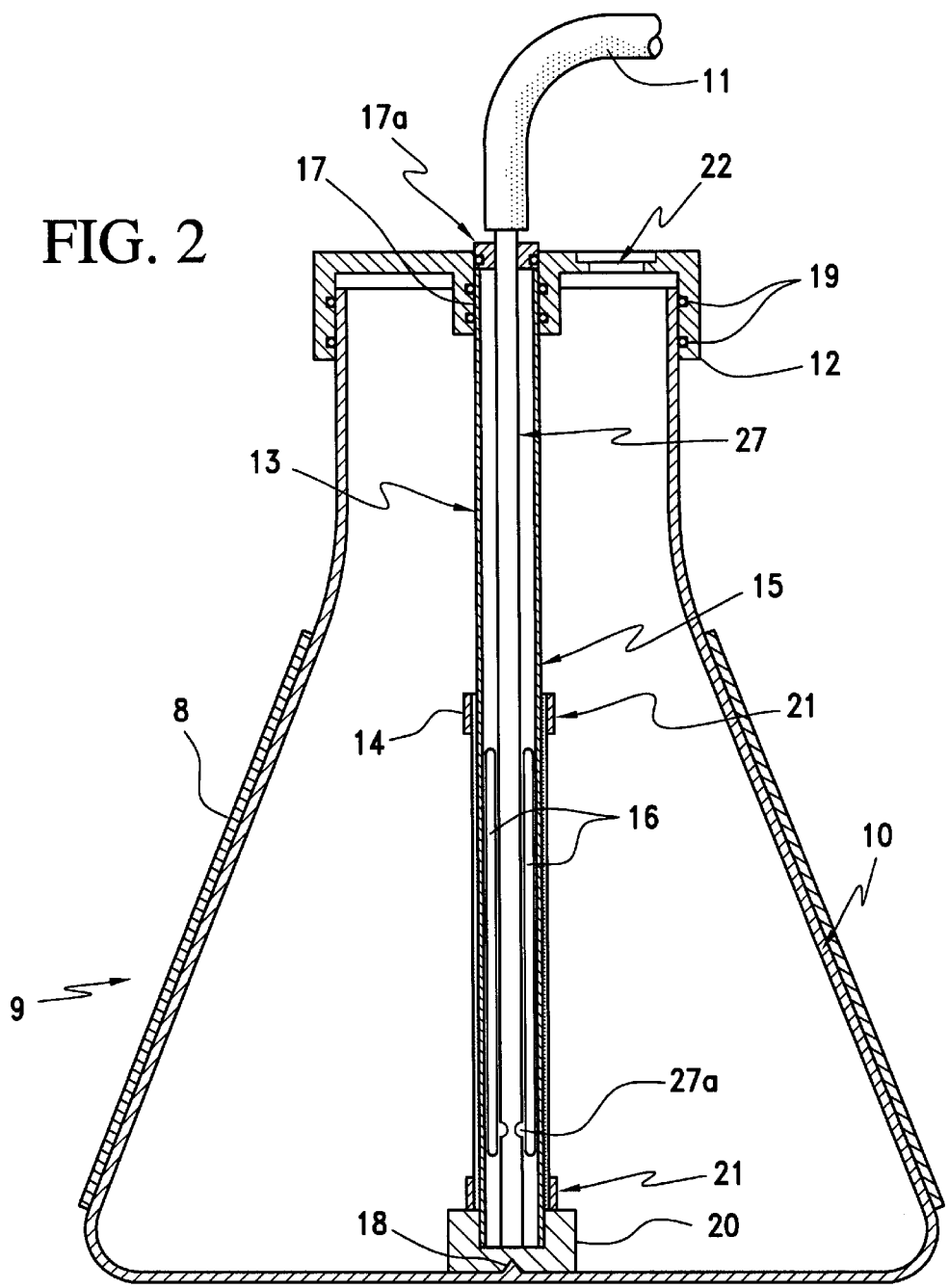
FIG. 2.
Figure 3:
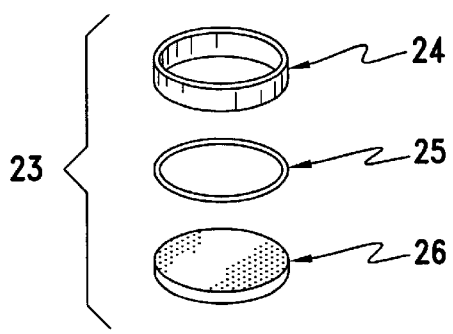
FIG. 3.

FIG. 2 illustrates the apparatus 9 of the invention. Bone is demineralized by placing bone, for example ground bone, in reaction vessel 10 containing a demineralization solution, for example one or more acids at a concentration sufficient to demineralize bone, and in a volume sufficient to process the amount of bone to be demineralized, for example from about 2.0 to about 8.0 liters, preferably from about 3.0 to about 6.0 liters of acid, optionally including heating blanket or thermal wrap 8. Thereafter, a defoaming agent is added to the vessel through tubing 11 connected to the vessel cap 12. Vessel cap 12 is connected to reaction vessel 10 via O-rings 19. The defoamer flows into reaction vessel 10 through filter tube assembly 13 including the filter mesh 14 disposed over the filter tube 15 having openings 16, and downtube 27 having openings 27a (at least two), the filter tube assembly 13 connected at it's top end to vessel cap 12 via a connection 17 and top end cap 17a, this connection can be a threaded connection, a frictional connection, a connection vial O-rings, or the equivalent; and connected at it's bottom end to end cap 20 via, for example, a press fit, a frictional fit, a threaded connection, or via O-rings or the equivalent. The filter tube assembly 13 at its bottom end is seated on protrusion 18 of reaction vessel 10. The keeper rings 21 serve to anchor filter mesh 14 to filter tube 15. The filter mesh 14 is composed of any material stable in the presence of the demineralizing solution, and include polyester or Teflon, or an equivalent material, and preferably has a mesh size of about 125μ. Suitable defoamers include any defoamers well known in the art to which the invention pertains, and include for example ethanol, for example 60 mls of 200 proof ethanol in 6.0 liters of acid. The bone-acid-ethanol solution is then preferably vigorously agitated, such agitation including for example orbital shaking at a rate sufficient to keep the bone particles in suspension, for example, at from about 20 to about 60 cycles per minute on an orbital shaker table, while the system is maintained at a desired temperature, for example of from about 15° C. to about 100° C., preferably from about 15° C. to about 50° C., more preferably from about 20° C. to about 40° C., and most preferably at about 23° C. After an initial period of time, for example, five minutes, substantially all, for example 90% to 95%, of the acid is then rapidly drained from vessel 10 through vessel cap 12 and tubing 11, via a vacuum pump connected to tubing 11, thus rapidly pulling the acid solution through filter mesh 14 covering filter tube 15 of filter assembly 13, and downtube 27 having openings 27a, and exiting the vessel 10 via tubing 11. Vessel 10 was then refilled with the demineralizing solution via tubing 11 connected to vessel cap 12 and flowing into vessel 10 through downtube 27 and filter mesh 14 covering filter tube 15 of filter assembly 13, and the contents of the vessel 10 was again agitated for a second period of time for example about ten minutes. The vessel 10 was optionally again rapidly drained, refilled and agitated for a third period of time, for example 20 minutes. The acid was then drained and a buffer solution was added to vessel 10 through tubing 11 connected to vessel cap 12 and filter assembly 13, to stop the demineralizing reaction. All of the components of apparatus 9 can be composed of any material stable in the presence of the demineralizing solution. Suitable materials include Teflon, glass, and ceramic. Vessel cap 12 further includes port 22 used to fill the reaction vessel 9, with bone. Thereafter, port filter assembly 23 illustrated in FIG. 3, including retaining ring 24, O-ring 25, and fritted filter 26, is place in the port to allow maintain the closed system during pulse and drain exchanges, gas can sterilely leave or enter vessel 10 via port filter assembly 23.

EXAMPLES

Example 1

Using a comparative continuous flow process, bone was recovered from nine cadaver donors. The bone was cleaned of soft tissue, bone marrow elements, lipid elements and undesirable constituents, and ground to a particle size of $250\mu$ to $710\mu$. The bone (400 grams) and a stir bar were placed into the inner vessel of a continuous flow demineralization apparatus. The apparatus was closed and placed onto an external stirring drive. The apparatus was filled with 0.5N hydrochloric acid with stirring. Once the apparatus was full, stirring and acid flow were adjusted to maintain the bone material in suspension and to achieve a linear change in the pH of the eluent acid with time and/or volume of acid pumped into the apparatus. The initial pH of eluent approximated pH 3.0+. The demineralization process was stopped, when the eluent solution pH was at about 1.2. This endpoint correlates to about 2.0 wt % residual calcium in the bone. The acid was then drained and the bone was washed with water until the pH of the bone was greater than 3.0. The pH of the bone was then adjusted to about pH 6.5 to 7.5 with sodium/potassium phosphate buffer.

The reaction rate of demineralization was 1.5 grams of bone per minute. It took about 330 minutes to demineralize 400 grams of bone. It was observed that the bone in the continuous flow system was not uniformly mixed when the bone mass neared 350 grams in the container. The bone caked and accumulated along the wall of the container during the first 85 minutes of demineralization. The constant flow of fresh 0.5N acid at a rate of 35 mls per minute was insufficient in that it was to small a volume and to poorly mixed with the bone.

Example 2

Using the inventive process and the inventive apparatus of FIG. 1, bone was recovered from cadaver donors. The bone was cleaned of soft tissue, bone marrow elements, lipid elements and undesirable constituents, and ground to a particle size of $250\mu$ to $710\mu$. 800 grams of bone (pooled sample 2) was placed into 6.0 liters of 0.5 N hydrochloric acid containing 60 mls of 200 proof ethanol as a defoamer for when carbon dioxide outgassing occurs. The bone-acid-ethanol solution was then vigorously stirred at 1350 rpm while the system was maintained at 23° C. 95% of the 6.0 liters of acid was then drained (drain) and the vessel was refilled (pulsed) at 5 minutes, 15 minutes, and 35 minutes. Samples of bone and bath acid were also removed from the vessel at these times. It was observed at the 5 minute time interval, the acid concentration was quickly consumed by the bone. At the end of only one hour the pH was returned to it's starting value of 0.58. The calcium concentration in each of the bone samples were determined by the DMA spectrophotometric method after the tissue was completely hydrolyzed in acid.

This 800 gram demineralization process had a reaction rate of 21.1 grams per minute versus the 1.5 grams per minute for the 400 gram continuous flow process. The pulse/drain process with high energy stirring achieved the 2 wt % residual calcium osteoinductivity target in 38 minutes. The continuous flow process took about 330 minutes to demineralize a bone mass of about 400 grams.

Example 3

Ground bone was demineralized according to the process set forth in Example 2, with the 0.5N HCL being replaced with 2.0M citric acid. Multi pulsed/drained demineralization using 2.0M citric acid resulted in the lowering of the ground bone's calcium concentration from 23.1% to 11.4% in 25 minutes. This result is surprising since citric acid is characterized as a weak acid by comparison to the strongly ionized hydrochloric acid.

Example 4

Using the inventive process and the inventive apparatus of FIG. 2, bone was recovered from cadaver donors. The bone was cleaned of soft tissue, bone marrow elements, lipid elements and undesirable constituents, and ground to a particle size of $125\mu$ to $850\mu$. 730 grams of bone (pooled sample 3) was placed into 4.0 liters of 0.5 N hydrochloric acid containing 40 mls of 70% IPA as a defoamer for when carbon dioxide outgassing occurs. The bone-acid-alcohol solution was then agitated at a setting of 200 on an orbital shaker Model No: 980001, by Troemner, Inc., at ambient temperature. 95% of the 4.0 liters of acid was then drained (drain); and the vessel was refilled (pulsed) and drained (drain) at 5 minute intervals with orbital shaking. Samples of bone and bath acid were also removed from the vessel at these times. It was observed at the 5 minute time interval, the acid concentration was quickly consumed by the bone. At the end of only one hour the pH was returned to it's starting value of 0.58. The calcium concentration in each of the bone samples were determined by the DMA spectrophotometric method after the tissue was completely hydrolyzed in acid.

This 730 gram demineralization process had a reaction rate of 21.1 grams per minute versus the 1.5 grams per minute for the 400 gram continuous flow process. The pulse/drain process with orbital shaking achieved the 2 wt % residual calcium osteoinductivity target in 38 minutes. The continuous flow process took about 330 minutes to demineralize a bone mass of about 400 grams.

All of the publications cited herein are hereby incorporated by reference into the present disclosure. It will be appreciated by those skilled in the art to which the invention pertains that various modifications can be made without departing from the essential nature thereof. It is intended to encompass all such modification within the scope of the appended claims.

We claim:

1. A rapid demineralization process for producing osteoinductive bone, comprising:
   subjecting bone to two or more pulse and drain exchanges of a predetermined volume of one or more demineralizing acid solutions to produce demineralized bone.

2. A rapid demineralization process for producing osteoinductive bone, comprising:
   subjecting bone to two or more pulse and drain exchanges of a predetermined volume of one or more demineralizing acid solutions under conditions effective to produce demineralized bone.

3. The rapid demineralization process of any one of claims 1 or 2, each of said pulse and drain exchanges comprising:
   rapidly pulsing a predetermined volume of one or more demineralizing acid solutions into said container;
   incubating said bone and said predetermined volume of one or more demineralizing acid solutions in said container for an interval of time; and rapidly draining said predetermined volume of one or more demineralizing acid solutions from said container.

4. A rapid demineralization process for producing osteoinductive demineralized bone, comprising:

placing an amount of bone to be demineralized into a substantially closed container;

and cycling said bone in said substantially closed container through two or more pulse and drain cycles to produce said osteoinductive demineralized bone, each of said two or more pulse and drain cycles, comprising:

rapidly pulsing a predetermined volume of one or more demineralizing acid solutions into said container;

incubating said bone and said one or more demineralizing acid solutions in said container for an interval of time; and rapidly draining said predetermined volume of one or more demineralizing acid solutions from said container.

5. The rapid demineralization process of any one of claims 1, 2, 3, or 4, wherein said bone is demineralized at a rate of from about 1.5 g/min. to about 30.0 g/min.

6. The rapid demineralization process of claim 5, said bone is demineralized at a rate of greater than 5.0 g/min.

7. The rapid demineralization process of claim 6, said bone is demineralized at a rate of greater than 8.0 g/min.

8. The rapid demineralization process of claim 7, said bone is demineralized at a rate of greater than 10.0 g/min.

9. The rapid demineralization process of claim 8, said bone is demineralized at a rate of grater than 15.0 g/min.

10. The rapid demineralization process of claim 9, said bone is demineralized at a rate of grater than 20.0 g/min.

11. The rapid demineralization process of any one of claims 1, 2, or 4, said pulse being carried out in less than 3.0 min.

12. The rapid demineralization process of any one of claims 1, 2, or 4, said drain being carried out in less than 6.0 min.

13. The rapid demineralization process of claim 11, said pulse being carried out in less than 2.0 min.

14. The rapid demineralization process of claim 12, said drain being carried out in less than 5.0 min.

15. The rapid demineralization process of any one of claims 3, or 4, said interval of time is from about 1.0 min. to about 30.0 min.

16. The rapid demineralization process of claim 15, said interval of time is from about 2.0 min. to about 20.0 min.

17. The rapid demineralization process of claim 16, said interval of time is from about 3.0 min to about 10.0 min.

18. The rapid demineralization process of claim 17, said interval of time is about 5.0 min.

19. The rapid demineralization process of any one of claims 3, or 4, said step of incubating comprising agitation.

20. The rapid demineralization process of claim 19, said agitation comprising stirring.

21. The rapid demineralization process of claim 19, said agitation comprising shaking.

22. The rapid demineralization process of claim 21, said shaking comprising shaking on an orbital shaker.

23. The rapid demineralization process of claim 20, said stirring comprising stirring at from about 1000 rpm to about 2000 rpm.

24. The rapid demineralization process of claim 23, said stirring comprising stirring at from about 1200 rpm to about 1500 rpm.

25. The rapid demineralization process of claim 22, said orbital shaking comprising orbital shaking at a rate of from about 20 cycles/min. to about 60 cycles/min.

26. The rapid demineralization process of claim 25, said orbital shaking comprising orbital shaking at a rate of from about 30 cycles/min. to about 50 cycles/min.

27. The rapid demineralization process of any one of claims 1, 2, 3, or 4, said process being carried out at a temperature of from about 0° to about 100° C.

28. The rapid demineralization process of claim 27, said process being carried out at a temperature of from about 15° C. to about 50° C.

29. The rapid demineralization process of claim 28, said process being carried out at a temperature of from about 20° C. to about 40° C.

30. The rapid demineralization process of claim 29, said process being carried out at a temperature of about 23° C.

31. The rapid demineralization process of any one of claims 1,2,3, or 4, said two or more pulse and drain exchanges comprise two pulse and drain exchanges.

32. The rapid demineralization process of any one of claims 1, 2, 3, or 4, said two or more pulse and drain exchanges comprise three pulse and drain exchanges.

33. The rapid demineralization process of any one of claims 1, 2, 3, or 4, said two or more pulse and drain exchanges comprise four pulse and drain exchanges.

34. The rapid demineralization process of any one of claims 1, 2, 3, or 4, said predetermined volume comprising 10.0 liters or less.

35. The rapid demineralization process of any one of claims 1, 2, 3, or 4, said predetermined volume comprising 8.0 liters or less.

36. The rapid demineralization process of any one of claims 1, 2, 3, or 4, said predetermined volume comprising 6.0 liters or less.

37. The rapid demineralization process of any one of claims 1, 2, 3, or 4, said predetermined volume comprises 4.0 liters.

38. A rapid demineralization process for demineralizing bone, comprising: subjecting bone to two or more rapid pulse and drain cycles of one or more acid solutions, where said bone is demineralized until a predetermined residual calcium level in said bone is achieved.

39. The rapid demineralization process of any one of claims 3, or 4, further comprising: stopping said demineralization process once a predetermined residual calcium level present in said bone is achieved.

* * * * *